| United States Patent [19] | [11] | 4,173,644 |
|---|---|---|
| Brown et al. | [45] | Nov. 6, 1979 |

[54] THIOUREA COMPOUNDS, COMPOSITIONS AND METHODS AND USE

[75] Inventors: Thomas H. Brown; Graham J. Durant; Charon R. Ganellin, all of Welwyn Garden City; Robert J. Ife, Stevenage, all of England

[73] Assignee: Smith Kline & French Laboratories Limited, Welwyn Garden City, England

[21] Appl. No.: 928,924

[22] Filed: Jul. 28, 1978

Related U.S. Application Data

[62] Division of Ser. No. 823,559, Aug. 11, 1977, Pat. No. 4,120,966, which is a division of Ser. No. 652,925, Jan. 27, 1976, Pat. No. 4,056,621.

[30] Foreign Application Priority Data

Feb. 3, 1975 [GB] United Kingdom ............... 4538

[51] Int. Cl.$^2$ ............... C07D 277/30; A61K 31/425
[52] U.S. Cl. ................... 424/270; 548/204; 548/205; 548/213; 548/214; 548/134; 548/135; 548/183; 548/186; 548/187
[58] Field of Search ......... 260/302 A, 302 D, 302 R; 424/270, 273

*Primary Examiner*—Donald G. Daus
*Assistant Examiner*—Lisa Jones
*Attorney, Agent, or Firm*—Joan S. Keps; Richard D. Foggio; William H. Edgerton

[57] ABSTRACT

The compounds are dithiocarbamates and isothioureas which are histamine $H_2$-antagonists. Two compounds of the invention are 2-(5-methyl-4-imidazolylmethylthio)ethyl N-methyldithiocarbamate and S-[2-(5-methyl-4-imidazolyl-methylthio)ethyl]-N-cyano-N'-methylisothiourea.

4 Claims, No Drawings

THIOUREA COMPOUNDS, COMPOSITIONS AND METHODS AND USE

This is a division of application Ser. No. 823,559, now U.S. Pat. No. 4,120,966 Aug. 11, 1977 which is a division of application Ser. No. 652,925, Jan. 27, 1976 now U.S. Pat. No. 4,056,621.

This invention relates to pharmacologically active compounds, to pharmaceutical compositions containing these compounds and to methods of blocking histamine $H_2$-receptors by administering these compounds. The compounds of the invention can exist as acid addition salts but, for convenience, reference will be made throughout this specification to the parent compound.

Many physiologically active substances elicit their biological actions by interaction with specific sites known as receptors. Histamine is such a substance and has a number of biological actions. Those biological actions of histamine which are inhibited by drugs commonly called "antihistamines" of which mepyramine is a typical example, and diphenhydramine and chlorpheniramine are other examples, are mediated through histamine $H_1$-receptors (Ash and Schild, Brit. J. Pharmac. Chemother., 27, 427, (1966). However, other of the biological actions of histamine are not inhibited by "antihistamines" and actions of this type which are inhibited by a compound described by Black et al. (Nature, 236, 385 (1972)) and called burimamide are mediated through receptors which are defined by Black et al. as histamine $H_2$-receptors. Thus histamine $H_2$-receptors may be defined as those histamine receptors which are not blocked by mepyramine but are blocked by burimamide. Compounds which block histamine $H_2$-receptors are referred to as histamine $H_2$-antagonists.

Blockade of histamine $H_2$-receptors is of utility in inhibiting the biological actions of histamine which are not inhibited by "antihistamines". Histamine $H_2$-antagonists are therefore useful, for example, as inhibitors of gastric acid secretion, as anti-inflammatory agents and as agents which act on the cardiovascular system, for example as inhibitors of the effects of histamine on blood pressure. In the treatment of certain conditions, for example inflammation and in inhibiting the actions of histamine on blood pressure, a combination of histamine $H_1$-and $H_2$-antagonists is useful.

The compounds of this invention are histamine $H_2$-antagonists. These compounds are represented by the following formula:

FORMULA 1

$$R_1-S-C\underset{NHR_2}{\overset{X}{\diagup\!\!\!\diagdown}}$$

wherein $R_1$ represents a grouping of the structure shown in Formula 2:

$$Het-CH_2S(CH_2)_2- \qquad \text{FORMULA 2}$$

wherein Het is a nitrogen-containing 5 or 6 membered heterocylic ring such as imidazole, pyridine, thiazole, isothiazole, or thiadiazole, which ring is optionally substituted by lower alkyl, lower alkoxy or halogen; $R_2$ is hydrogen, lower alkyl or the same as $R_1$; X is sulphur, $=NH$ or $=NCN$.

Throughout the present specification, by the term "lower alkyl" we mean an alkyl group containing from 1 to 4 carbon atoms, preferably methyl, and by the term "lower alkoxy" we mean an alkoxy group containing from 1 to 4 carbon atoms, preferably methoxy. It will be understood that the structure illustrated in Formula 1 is only one of several representations and that other tautomeric forms are also covered by the present invention. Hydrates, pharmaceutically acceptable salts, and hydrated pharmaceutically acceptable salts of compounds of Formula 1 are also covered by the present invention.

Preferably Het is a 4-imidazolyl ring optionally substituted by halogen or lower alkyl, a 2-thiazolyl ring, a 3-isothiazolyl ring optionally substituted by halogen, or a 2-pyridyl ring optionally substituted by lower alkyl, halogen or lower alkoxy.

Particularly preferably Het is a 5-methyl-4-imidazolyl ring.

Examples of specific compounds falling within the scope of the present invention are 2-(5-methyl-4-imidazolylmethyl-thio)ethyl N-methyldithiocarbamate, S-[2-(5-methyl-4-imidazolylmethylthio)ethyl]-N-cyano-N'-methylisothiourea, S-[2-(5-methyl-4-imidazolylmethylthio)ethyl]isothiourea and S-(2-(5-methyl-4-imidazolylmethylthio)ethyl)dithiocarbamate.

Compounds of Formula 1 may be prepared by treating a compound of Formula 3:

FORMULA 3

$$AS-\overset{\overset{\displaystyle X}{\|}}{C}-NHR_2$$

wherein X and $R_2$ have the same significance as in Formula 1 and A represents a lower alkyl group, with a mercaptan of Formula 4:

$$R_1SH \qquad \text{FORMULA 4}$$

wherein $R_1$ is as defined in Formula 1. Preferably this reaction is carried out in a solvent, such as pyridine, and at elevated temperatures e.g., 100° C.

The mercaptans of Formula 4 may be prepared by the reaction of ethanedithiol with a compound of Formula 5, in which Het has the same significance as in Formula 2, and Y represents chlorine or bromine.

$$Het-CH_2-Y \qquad \text{FORMULA 5}$$

Preferably this reaction is carried out in a solvent in the presence of a base, such as with sodium ethoxide in dry ethanol.

Compounds of Formula 1 wherein X is sulphur may be prepared alternatively by the reaction of a mercaptan of Formula 4 with an isothiocyanate of formula $R_2NCS$, $R_2$ being as defined in Formula 1. Preferably this reaction is carried out in a solvent such as pyridine.

The compounds of Formula 1 wherein X is sulphur and $R_2$ is hydrogen may also be prepared by treating a thiocyanate of formula $R_1SCN$, $R_1$ being as defined in Formula 1 with hydrogen sulphide. This reaction is preferably carried out at low temperature in a solvent such as ethanol. The thiocyanates may conveniently be prepared by treating a compound of the formula $R_1Y$, wherein $R_1$ is as defined in Formula 1 and Y is chlorine or bromine, with potassium thiocyanate.

Compounds of Formula 1 wherein X is $=NH$ may be prepared alternatively by treating a compound of Formula 6:

FORMULA 6

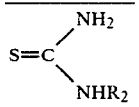

wherein $R_2$ is as defined in Formula 1, with a compound of Formula $R_1Y$ where $R_1$ is as defined in Formula 1 and Y is chlorine or bromine. The compounds of formula $R_1Y$ may be prepared from the corresponding alcohols of formula $R_1OH$ by standard techniques, e.g., the chlorides may be prepared from the corresponding alcohols by treatment with thionyl chloride.

The alcohols of formula $R_1OH$ may be prepared by the reaction of mercaptoethanol with a compound of formula $HetCH_2Y$, in which Het has the same significance as in Formula 2 and Y represents chlorine or bromine. Preferably this reaction is carried out in a solvent in the presence of a base, such as with sodium ethoxide in dry ethanol.

The compounds of Formula 1 block histamine $H_2$-receptors, that is they inhibit the biological actions of histamine which are not inhibited by "antihistamines" such as mepyramine but are inhibited by burimamide. For example, the compounds of this invention have been found to inhibit histamine-stimulated secretion of gastric acid from the lumen-perfused stomachs of rats anaesthetized with urethane, at doses of from 0.5 to 256 micromoles per kilogram intravenously. This procedure is referred to in the above mentioned paper of Ash and Schild. The activity of these compounds as histamine $H_2$-antagonists is also demonstrated by their ability to inhibit other actions of histamine which, according to the above mentioned paper of Ash and Schild, are not mediated by histamine $H_1$-receptors. For example, they inhibit the actions of histamine on the isolated guinea pig atrium and isolated rat uterus.

The compounds of this invention inhibit the basal secretion of gastric acid and also that stimulated by pentagastrin or by food.

In addition, the compounds of this invention show anti-inflammatory activity in conventional tests such as the rat paw oedema test, where the oedema is induced by an irritant, the rat paw volume is reduced by subcutaneous injection of doses of about 500 micromoles/kg of a compound of Formula 1.

In a conventional test, such as the measurement of blood pressure in the anaesthetised cat, the action of the compounds of this invention in inhibiting the vasodilator action of histamine can also be demonstrated. The level of activity of the compounds of this invention is illustrated by the effective dose producing 50% inhibition of gastric acid secretion in the anaesthetized rat and the dose producing 50% inhibition of histamine-induced tachycardia in the isolated guinea pig atrium.

For therapeutic use, the pharmacologically active compounds of the present invention will normally be administered as a pharmaceutical composition comprising as the or an essential active ingredient at least one such compound in the basic form or in the form of an addition salt with a pharmaceutically acceptable acid and in associated with a pharmaceutical carrier therefor. Such addition salts include those with hydrochloric, hydrobromic, hydriodic, sulphuric and maleic acids and may conveniently be formed from the corresponding bases of Formula 1 by standard procedures, for example by treating the base with an acid in a lower alkanol or by the use of ion exchange resins to form the required salt either directly from the base or from a different addition salt.

Pharmaceutical compositions comprising a pharmaceutical carrier and a compound of Formula 1 or a pharmaceutically acceptable acid addition salt thereof and methods of blocking histamine $H_2$-receptors which comprise administering a compound of Formula 1 or a pharmaceutically acceptable acid addition salt thereof are also objects of this invention. The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like.

A wide variety of pharmaceutical forms can be employed. Thus, if a solid carrier is used, the preparation can be tableted, placed in a hard gelatin capsule in powder or pellet form, or in the form of a troche or lozenge. The amount of solid carrier will vary widely but preferably will be from about 25 mg to about 1 g. If a liquid carrier is used, the preparation may be in the form of a syrup, emulsion, soft gelatin capsule, sterile injectable liquid contained for example in an ampoule, or an aqueous or nonaqueous liquid suspension.

The pharmaceutical compositions are prepared by conventional techniques involving procedures such as mixing, granulating and compressing or dissolving the ingredients as appropriate to the desired preparation.

The active ingredient will be present in the composition in an effective amount of block histamine $H_2$-receptors. The route of administration may be oral or parenteral.

Preferably, each dosage unit will contain the active ingredient in an amount of from about 50 mg to about 250 mg.

The active ingredient will preferably be administered one to six times per day. The daily dosage regimen will preferably be from about 150 mg to about 1500 mg.

Advantageously the composition will be made up in a dosage form appropriate to the desired mode of administration, for example as a tablet, capsule, injectable solution or as a cream or ointment for topical application.

The invention is illustrated and in no way limited by the following examples wherein all temperatures are given in degrees Centigrade:

EXAMPLE 1

2-(5-Methyl-4-imidazolylmethylthio)ethyl N-methyl-dithiocarbamate dithiocarbamate (a) Sodium (5.2 g) was added, with stirring under nitrogen, to dry ethanol (150 ml). After the sodium had dissolved ethanedithiol (40 ml) was introduced and to this mixture was added 4-methyl-5-chloromethylimidazole hydrochloride (15 g), as a solid, over a period of 1.5 hours at room temperature. The mixture was then stirred for a further 1 hour at room temperature. After this time a saturated solution of hydrogen chloride in ethanol was added until the mixture was acidic. The temperature was then raised and the ethanol distilled off under nitrogen. The residue was taken up in water and continuously extracted with ether to remove the excess etanedithiol. The aqueous fraction was then evaporated to dryness and the residue extracted with hot isopropanol. Reducing the volume of the extract and cooling afforded 2-(5-methyl-4-imidazolyl-methyl-thio)ethanethiol hydrochloride as a white solid which was not purified further.

(b) A solution of sodium carbonate was added to s solution of 2-(5-methyl-4-imidazolylmethylthio)ethanethiol hydrochloride (2.8 g) in water (50 ml) to pH9 and the mixture extracted with ethyl acetate. After drying ($MgSO_4$), the extract was evaporated to dryness and the residue taken up in pyridine (25 ml). To this solution was added methylisothiocyanate(1.1 g) and the mixture stirred at room temperature for 1 hour. After this time the mixture was evaporated to give the crude title product. This residue was taken up in ethanol and a saturated solution of hydrogen chloride in ethanol added until the mixture was acidic. Addition of ether to this solution afforded a white solid which after repeated recrystallisation from ethanol/ether gave 2-(5-methyl-4-imidazolylmethylthio)ethyl-N-methyldithiocarbamate hydrochloride, m.p. 171°–172°.

(Found: C, 36.5; H, 5.3; N, 14.1; S, 31.9; Cl, 12.2; $C_9H_{15}N_3S_3$·HCl requires; C, 36.3; H, 5.4; N, 14.1; S, 32.3; Cl, 11.9%)

This hydrochloride may be treated with aqueous sodium carbonate and the mixture extracted with chloroform and the chloroform extracts evaporated to give the free base.

EXAMPLE 2

S-[2-(5-Methyl-4-imidazolylmethylthi0)ethyl]-N-cyano-N'-methylisothiourea 2-(5-Methyl-4-imidazolylmethylthio)ethanethiol (4.0 g) (prepared from the hydrochloride as in Example 1(b)) and N-cyano-N', S-dimethylisothiourea (4.0 g) were heated together under nitrogen in pyridine (100 ml) at 100° for 20 hours. After this time the mixture was evaporated to dryness to give the crude title product. This residue taken up in water acidified to pH2 with concentrated hydrochloric acid. After extracting with ethyl acetate the volume of the aqueous fraction was reduced and on cooling gave S-[2-(5-methyl-4-imidazolylmethylthio)-ethyl]-N-cyano-N'-methylisothiourea hydrochloride, m.p. 225°.

(Found: C, 39.3; H, 5.4; N, 23.1; S, 21.2; Cl, 11.7; $C_{10}H_{15}N_5S_2$. HCl requires; C, 39.3; H, 5.2; N, 23.0; S, 21.0; Cl, 11.6%).

This hydrochloride may be treated with aqueous sodium carbonate and the mixture extracted with chloroform and the chloroform extracts evaporated to give the free base.

EXAMPLE 3

S-[2-(5-Methyl-4-imidazolylmethylthio)ethyl]isothiourea (a) Sodium (3.0 g) was added, with stirring under nitrogen, to dry ethanol (75 ml). After the sodium had dissolved mercaptoethanol (9.0 ml) was introduced and to this mixture was added 4-methyl-5-chloromethylimidazole hydrochloride (10 g), as a solid, over a period of 1.5 hours at room temperature. The mixture was then stirred for a further 1 hour at room temperature. After this time the reaction was warmed and the ethanol distilled off at reduced pressure. The residue was taken up in water, acidified with concentrated hydrochloric acid, and continuously extracted with ether to remove the excess mercaptoethanol. The aqueous fraction was then basified using solid sodium carbonate and continuously extracted with ethyl acetate. To the extract was added a further volume of ethyl acetate and the whole warmed to re-dissolve the crude product which had deposited. After drying ($MgSO_4$) and reducing the volume, crystallisation from this solution below 40° and cooling to −15° afforded 2-(5-methyl-4-imidazolylmethylthio)ethanol, m.p. 74°–76°.

(Found: C, 49.1; H, 6.8; N, 16.2: $C_7H_{12}N_2O$ S requires: C, 48.8; H, 7.0; N, 16.3%).

(b) 2-(5-Methyl-4-imidazolylmethylthio)ethanol (0.34 g, 2 mmol) and thionyl chloride (0.238 g, 2 mmol) were heated together, with stirring, at reflux temperature in chloroform (10 ml) for one hour, giving a grey solution and a green oil. A second equivalent of thionyl chloride (0.238 g) was added at reflux temperature and immediately the oil went into solution and a solid started to crystallise. After a further 15 minutes at reflux temperature the mixture was cooled and the solid collected (0.395 g). Recrystallisation from acetonitrile gave 1-chloro-2-(5-methyl-4-imidazolylmethylthio)ethane hydrochloride, m.p. 163°–165°, (0.29 g).

(Found: C, 37.1; H, 5.2; N, 12.6; S, 14.1; Cl, 31.2: $C_7H_{11}Cl\ N_2S$ requires: C, 37.0; H, 5.3; N, 12.3; S, 14.1: Cl, 31.2%).

(c) 1-Chloro-2-(5-methyl-4-imidazolylmethylthio)ethane hydrochloride (3.9 g, 17 mmol) and thiourea (1.30 g, 17 mmol) were heated together at reflux temperature for 48 hours in ethanol (50 ml). After cooling the ethanol was evaporated to give the crude title product as an oil. This oil was converted to the sulphate salt by dissolution in water (220 ml) and passage down an ion-exchange column. The water was evaporated and the residual oil triturated with boiling methanol to give a white solid (4.33 g). Crystallisation of this solid from aqueous methanol gave S-[2-(5-methyl-4-imidazolylmethylthio)ethyl]isothiouronium sulphate (3.70 g), m.p. 217°–220°.

(Found: C, 29.4; H, 5.1; N, 17.1; S, 29.0; $C_8H_{14}N_4S_2$·$H_2SO_4$. requires: C, 29.3; H, 4.9; N, 17.1; S, 29.3%).

This sulphate may be treated with aqueous sodium carbonate and the mixture extracted with chloroform and the chloroform extracts evaporated to give the free base.

EXAMPLE 4

S-[2-(5-Methyl-4-imidazolylmethylthio)ethyl]dithiocarbamate (i) 1-Chloro-2(5-methyl-4-imidazolylmethylthio)ethane hydrochloride (2.1 g) and potassium thiocyanate (0.97 g) were heated together under reflux in ethanol (50 ml) for 3 days. The mixture was evaporated to dryness and the residue was taken up in water, basified with sodium carbonate and extracted with chloroform. The chloroform extracts were dried ($MgSO_4$) and evaporated to a residue which was recrystallised from acetonitrile to give 2-(5-methyl-4-imidazolylmethylthio)ethylthiocyanate m.p. 101°–103°. (Found: C, 45.3; H, 5.3; N, 19.5; S, 29.3. $C_8H_{11}N_3S_2$ requires: C, 45.0; H, 5.2; N, 19.7; S, 30.1%).

(ii) Hydrogen sulphide was passed for 1 hour at a pressure of 15 cm.Hg above atmospheric into a solution of 2-(5-methyl-4-imidazolylmethylthio)ethyl thiocyanate (2.0 g) in ethanol (20 ml) at −15°. Ethanolic hydrogen chloride was added followed by ether. The crude solid was taken up in water, treated with concentrated aqueous sodium carbonate and the mixture was extracted with chloroform. The chloroform extracts were dried and evaporated and the residue was purified by column chromatography (silica gel/5% methanol in chloroform) to give S-[2-(5-methyl-4-imidazolylmethylthio)ethyl]dithiocarbamate. Reconversion to the hydrochloride by treatment with ethanolic hydrogen chloride and recrystallisation from ethanol afforded S-[2-(5-methyl-4-imidazolylmethylthio)ethyl]dithiocarbamate hydrochloride, m.p. 191°–193°.

(Found: C, 34.1; H, 5.0; N, 14.9; S, 32.2; Cl, 12.3: $C_8H_{13}N_3S_3.HCl$ requires: C, 33.8; H, 5.0; N, 14.8; S, 33.9; Cl, 12.5%)

EXAMPLE 5

N,S-bis[2-(5-Methyl-4-imidazolylmethylthio)ethyl]-N'-cyanoisothiourea 2-(5-Methyl-4-imidazolylmethylthio)ethanethiol and N-cyano-N'-[2-(5-methyl-4-imidazolylmethylthio)ethyl]-S-methylisothiourea are heated together under nitrogen in pyridine at 100° for 20 hours and the mixture evaporated to give the crude title product. This residue is treated with hydrochloric acid to yield the hydrochloride of the title product.

EXAMPLE 6

N,S-bis[2-(5-Methyl-4-imidazolylmethylthio)ethyl]isothiourea

1-Chloro-2-(5-methyl-4-imidazolylmethylthio)ethane and N-[2-(5-methyl-4-imidazolylmethylthio)ethyl]thiourea are heated together at reflux temperature in ethanol, and the mixture is evaporated and the residue purified to give the title compound, which may be converted into a suitable salt by ion-exchange chromatography.

EXAMPLE 7

Substitution of:
(a) 4-(chloromethyl)imidazole
(b) 2-(chloromethyl)thiazole
(c) 3-(bromomethyl)isothiazole
(d) 4-bromo-3-(bromomethyl)isothiazole
(e) 2-(chloromethyl)-3-methylpyridine or salts thereof for 4-chloromethyl-5-methylimidazole hydrochloride in the procedure of Example 1 leads to the production of:
(a) 2-(4-imidazolylmethylthio)ethyl N-methyldithiocarbamate
(b) 2-(2-thiazolylmethylthio)ethyl N-methyldithiocarbamate
(c) 2-(3-isothiazolylmethylthio)ethyl N-methyldithiocarbamate
(d) 2-(4-bromo-3-isothiazolylmethylthio)ethyl N-methyldithiocarbamate
(e) 2-(3-methyl-2-pyridylmethylthio)ethyl N-methyldithiocarbamate and conversion of the above-mentioned halomethyl derivatives to the corresponding methylthioethylthiols by the procedure described in Example 1 followed by treatment with N-cyano-N',S-dimethylisothiourea according to the procedure of Example 2 leads to the production of:
(a) S-[2-(4-imidazolylmethylthio)ethyl]-N-cyano-N'-methylisothiourea
(b) S-[2-(2-thiazolylmethylthio)ethyl]-N-cyano-N'-methylisothiourea
(c) S-[2-(3-isothiazolylmethylthio)ethyl]-N-cyano-N'-methylisothiourea
(d) S-[2-(4-bromo-3-isothiazolylmethylthio)ethyl]-N-cyano-N'-methylisothiourea
(e) S-[2-(3-methyl-2-pyridylmethylthio)ethyl]-N-cyano-N'-methylisothiourea

EXAMPLE 8

(a)
(i) 3-Hydroxy-2-hydroxymethylpyridine (4.4 g) was added to a solution of sodium (0.81 g) in methanol (50 ml). The solvent was evaporated off, treated with toluene, reevaporated and taken up in dimethylsulphoxide (88 ml) to which was added methyl iodide (5.0 g) in dimethylsulphoxide (12 ml) while the solution was stirred for 30 minutes at 18°. After stirring overnight, the solvent was removed and the residue was partitioned between chloroform and water. The chloroform extract was evaporated and a solution of the residue in ethanol was treated with ethanolic hydrogen chloride to yield 2-hydroxymethyl-3-methoxypyridine hydrochloride (3.0 g) m.p. 208° dec. 2-Hydroxymethyl-3-methoxypyridine (4.2 g) was dissolved in chloroform (60 ml) and to the stirred solution was added thionyl chloride (6 ml). After stirring for 90 minutes and evaporation of the solvent, the residue was recrystallised from ethanol/ether to give 2-chloromethyl-3-methoxypyridine hydrochloride (5.1 g), m.p. 171.5°–172.5°.

(ii) A solution of sodium nitrite (2.38 g) in water (10 ml) was added dropwise to a mixture of 3-amino-2-hydroxymethylpyridine (4.8 g), aqueous hydrochloric acid (48%, 10 ml) and water (5 ml) stirred at 0°–5°. This solution was added to a hot solution of cuprous chloride (2.5 g) in conc. hydrochloric acid and the mixture was heated on a steam-bath for 0.5 hours, diluted with water and saturated with hydrogen sulphide. The mixture was filtered, concentrated and extracted with chloroform and the chloroform extract was evaporated to give 3-chloro-2-hydroxymethylpyridine (3.7 g) m.p. 42°–44° (from n-pentane).

(iii) 3-Chloro-2-hydroxymethylpyridine, 3-bromo-2-hydroxymethylpyridine and 4-bromo-5-hydroxymethylimidazole may be converted into 3-chloro-2-chloromethylpyridine, 3-bromo-2-chloromethylpyridine and 4-bromo-5-chloromethylimidazole by treatment with thionyl chloride as described above.

(b) Substitution of:
(a) 2-Chloromethyl-3-methoxypyridine
(b) 3-Chloro-2-chloromethylpyridine
(c) 3-Bromo-2-chloromethylpyridine
(d) 4-Bromo-5-chloromethylimidazole or salts thereof for 4-chloromethyl-5-methylimidazole hydrochloride in the procedure of Example 1 leads to the production of:
(a) 2(3-methoxy-2-pyridylmethylthio)ethyl N-methyldithiocarbamate
(b) 2-(3-chloro-2-pyridylmethylthio)ethyl N-methyldithiocarbamate
(c) 2-(3-bromo-2-pyridylmethylthio)ethyl N-methyldithiocarbamate
(d) 2-(5-bromo-4-imidazolylmethylthio)ethyl N-methyldithiocarbamate and conversion of the above-mentioned chloromethyl derivatives to the corresponding methylthioethylthiols by the procedure described in Example 1 followed by treatment with N-cyano-N',S-dimethylisothiourea according to the procedure of Example 2 leads to the production of:

(a) S-[2-(3-methoxy-2-pyridylmethylthio)ethyl]-N-cyano-N'-methylisothiourea
(b) S-[2-(3-chloro-2-pyridylmethylthio)ethyl]-N-cyano-N'-methylisothiourea
(c) S-[2-(3-bromo-2-pyridylmethylthio)ethyl]-N-cyano-N'-methylisothiourea
(d) S-[2-(5-bromo-4-imidazolylmethylthio)ethyl]-N-cyano-N'-methylisothiourea

EXAMPLE 9

| Ingredients | Amounts |
| --- | --- |
| S-[2-(5-methyl-4-imidazolylmethylthio)ethyl]-N-cyano-N'-methylisothiourea hydrochloride | 150 mg. |
| Sucrose | 75 mg. |
| Starch | 25 mg. |
| Talc | 5 mg. |
| Stearic Acid | 2 mg. |

The ingredients are screened, mixed and filled into a hard gelatin capsule.

EXAMPLE 10

| Ingredients | Amounts |
| --- | --- |
| S-[2-(5-methyl-4-imidazolylmethylthio)ethyl]-N-cyano-N'-methylisothiourea hydrochloride | 200 mg. |
| Lactose | 100 mg. |

The ingredients are screened, mixed and filled into a hard gelatin capsule.

EXAMPLE 11

2-(5-Methyl-4-imidazolylmethylthio)ethyl N-[2-(5-methyl-4-imidazolylmethylthio)ethyldithiocarbamate.

(i) A solution of 2((5-methyl-4-imidazolyl)methylthio)ethylamine (3.42 g, 0.02 mol) in dry pyridine (15 ml) was slowly added under dry nitrogen to a stirred solution of dicyclohexylcarbodiimide (4.12 g, 0.02 mol) and carbon disulphide (20 ml) in dry pyridine (10 ml) at $-10°$. After being stirred for 4 hours at $-10°$ then 18 hours at room temperature the cooled (0°) reaction mixture was filtered from dicyclohexylthiourea which was washed with ether. The combined filtrate and washings were evaporated under reduced pressure to dryness, traces of pyridine being removed by azeotropic distillation with water (50 ml) then isopropanol (50 ml). The residue was heated with acetonitrile (25 ml) and cooled to 0°, filtered and the filtrate was heated with excess ethanolic hydrogen chloride, then evaporated again to dryness. Recrystallisation of the residue from acetonitrile gave 5-methyl-4-(2-isothiocyanatoethylthiomethyl)imidazole hydrochloride (2.5 g) m.p. 150°–151°.

(Found: C, 38.6; H, 5.1; N, 17.0; S, 25.5; Cl; 14.1; $C_8H_{11}N_3S_2$. HCl requires; C, 38.5; H, 4.8; N, 16.8; S, 25.7; Cl, 14.2%)

(ii) 5-Methyl-4-(2-isothiocyanatoethylthiomethyl)imidazole hydrochloride may be treated with one equivalent of triethylamine and 2-(5-methyl-4-imidazolylmethylthio)ethanethiol according to the general procedure of Example 1(b) to give the title product.

EXAMPLE 12

S-[2-((1,2,5-Thiadiazol-3-yl)methylthio)ethyl]-N-cyano-N'-methylisothiourea (1) A mixture of N-bromosuccinimide (18.0 g), 4-methyl-1,2,5-thiadiazole (10.0 g), benzoyl peroxide (0.1 g) and carbon tetrachloride (250 mls) was illuminated by a 350 watt bulb and boiled under reflux for 5 hours. The mixture was left overnight at room temperature, filtered, and the filtrate was evaporated and distilled to give 3-bromomethyl-1,2,5-thiadiazole (6.4 g) b.p. 98°–115°/16 mm. This material may be purified by preparative gas-liquid chromatography.

(2) Conversion of 3-bromomethyl-1,2,5-thiadiazole into 2-((1,2,5-thiadiazol-3-yl)methylthio)ethane thiol by the procedure of Example 1 and treatment of this product with N-cyano-N',S-dimethylisothiourea according to the procedure of Example 2 leads to the production of the title compound.

What is claimed is:

1. A compound of the formula:

$$R_1-S-C{\overset{\displaystyle X}{\underset{\displaystyle NHR_2}{\nearrow\atop\searrow}}}$$

wherein $R_1$ represents a grouping of the structure
Het—$CH_2S(CH_2)_2$— wherein Het is a thiazole, isothiazole, or thiadiazole ring, which ring is optionally monosubstituted or disubstituted by lower alkyl, lower alkoxy or halogen $R_2$ is hydrogen, lower alkyl or the same as $R_1$; X is sulphur, =NH or =NCN; or a hydrate or pharmaceutically acceptable acid addition salt or hydrated salt thereof.

2. A compound of claim 1 wherein Het is a 2-thiazolyl ring or a 3-isothiazolyl ring optionally substituted by halogen, or a hydrate or pharmaceutically acceptable acid addition salt or hydrated salt thereof.

3. A pharmaceutical composition to block histamine $H_2$ receptors comprising in an effective amount to block said receptors a compound of claim 1 in combination with a pharmaceutically acceptable diluent or carrier.

4. A method of blocking histamine $H_2$-receptors which comprises administering to an animal in an effective amount to block said receptors a compound of claim 1.

* * * * *